US00PP24754P3

(12) United States Plant Patent
Harris

(10) Patent No.: US PP24,754 P3
(45) Date of Patent: Aug. 12, 2014

(54) AZALEA PLANT NAMED 'MNIHAR023'

(50) Latin Name: ***Rhododendron* sp.**
Varietal Denomination: MNIHAR023

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 64 days.

(21) Appl. No.: 13/506,321

(22) Filed: Apr. 11, 2012

(65) Prior Publication Data

US 2013/0276185 P1 Oct. 17, 2013

(51) Int. Cl.
*A01H 5/00* (2006.01)

(52) U.S. Cl.
USPC ..... Plt./238

(58) Field of Classification Search
CPC ..... A01H 5/02
USPC ..... Plt./238, 239
See application file for complete search history.

*Primary Examiner* — June Hwu
(74) *Attorney, Agent, or Firm* — Jondle Plant Sciences Division of Swanson & Bratschun, L.L.C.

(57) ABSTRACT

A new and distinct variety of azalea plant with spring and sporadic fall blooming, attractive, showy, single light peach with a light greenish center flowers, easily propagated by semi-hardwood cuttings in late spring through summer, moderate growth rate under normal fertilization and moisture conditions; compact, dense, broadly globose and freely branching in habit, grows well in containers, thrives in shade or sun and is hardy in Zone 7, is disclosed.

2 Drawing Sheets

Genus and species: *Rhododendron* sp.
Variety denomination: 'MNIHAR023'.

BACKGROUND OF THE NEW PLANT

The present invention is a new and distinct variety of evergreen azalea of the genus *Rhododendron*. This new azalea, hereinafter referred to as 'MNIHAR023', originated from a planned cross hybridization in a controlled environment in Lawrenceville, Ga. in 2004. The parental records of 'MNIHAR023' are unavailable. The present invention has a blooming period of late April thru mid May and sporadically starting in October continuing until frost. 'MNIHAR023' has a compact, dense, broadly globose growth habit, and cold hardiness.

The new plant was first propagated via semi-hardwood cuttings in 2006 in Dearing, Ga. and has been asexually reproduced repeatedly by semi-hardwood cuttings in Dearing, Ga. for over 4 years and five generations. 'MNIHAR023' has been found to retain its distinctive characteristics through successive asexual propagations via semi-hardwood cuttings.

Plant Breeder's Rights for this variety have not been applied for. 'MNIHAR023' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Dearing, Ga.

1. Spring and sporadic fall flowers;
2. Attractive, showy, light peach with a light greenish center flowers;
3. Numerous single flowers;
4. Easily propagated by semi-hardwood cuttings in late spring through summer;

5. Moderate growth rate under normal fertilization and moisture conditions;
6. Compact, dense, broadly globose and freely branching growth habit;
7. Grows well in containers;
8. Thrives in shade or sun; and
9. Hardy in Zone 7.

DESCRIPTION OF THE PHOTOGRAPHS

This new azalea variety is illustrated by the accompanying photographs. The colors shown are as true as can be reasonably obtained by conventional photographic means. The photographs are of four and five-year-old plants grown in filtered shade and full sun in 2010 and 2011 in Dearing, Ga.

DETAILED BOTANICAL DESCRIPTION OF THE NEW PLANT

Figure 1:
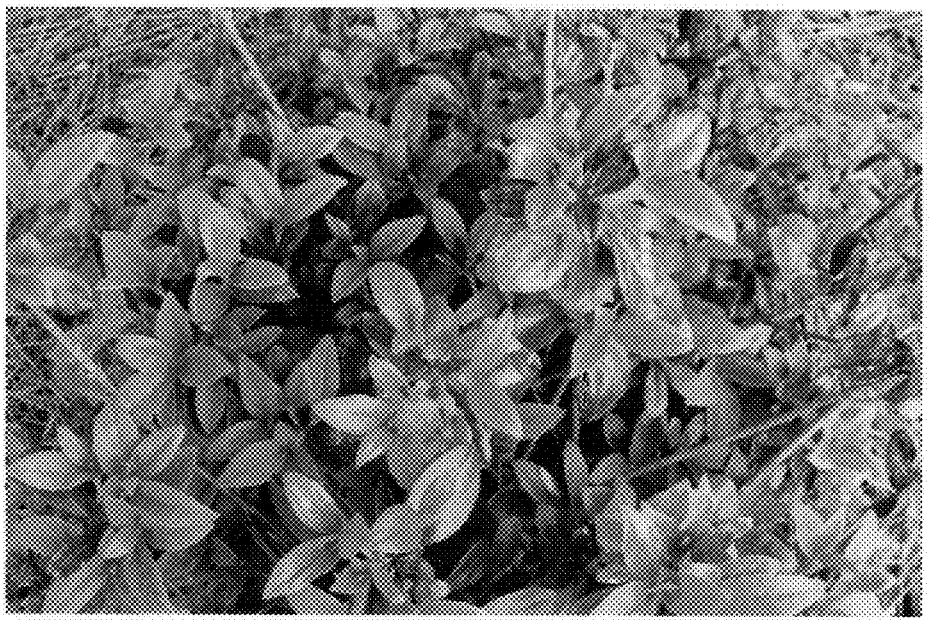
FIG. 1 is a close-up showing mature and immature foliage.
Figure 2:
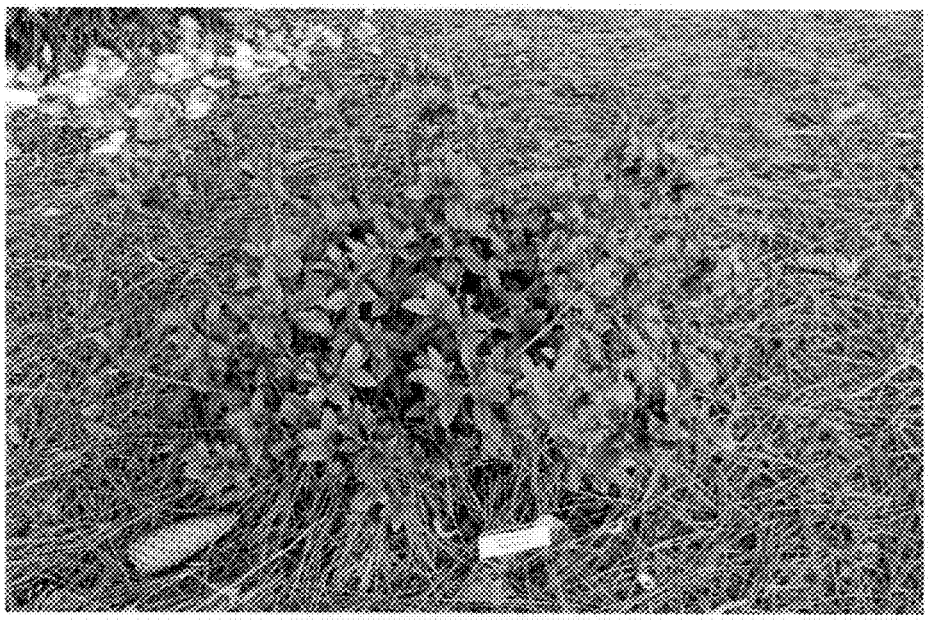
FIG. 2 shows mature foliage and growth habit of a five year old plant.
Figure 3:
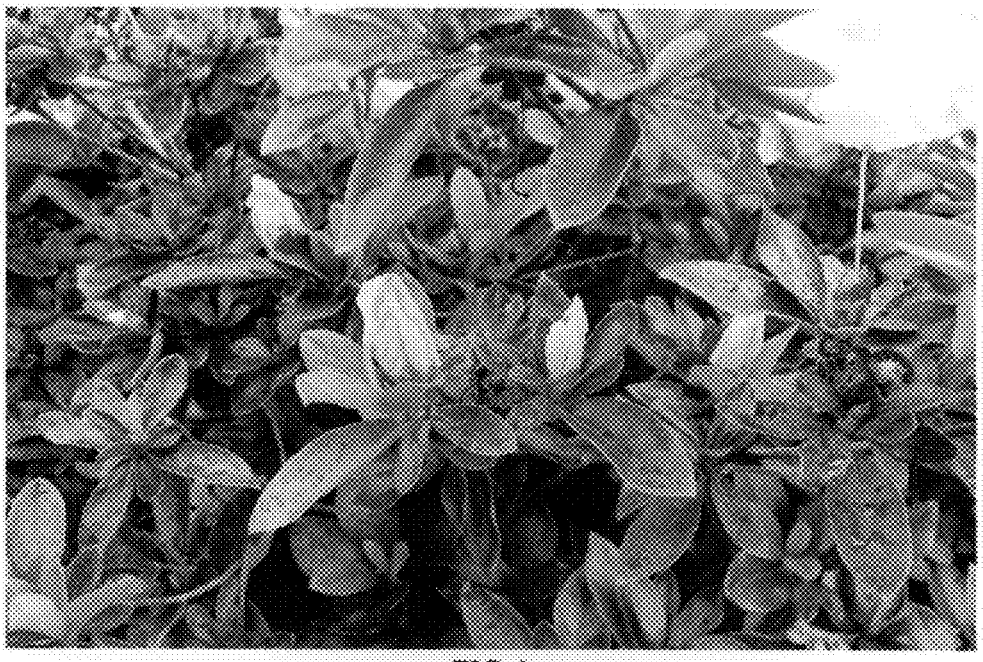
FIG. 3 is a close-up showing flower buds.
Figure 4:
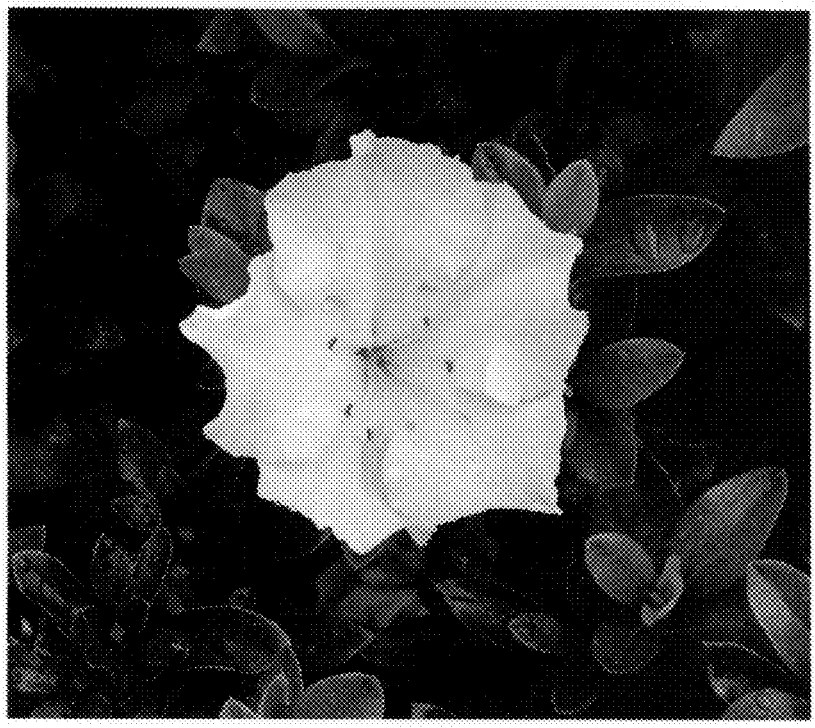
FIG. 4 is a close-up showing flower size, form, and color.

The following is a detailed description of the new variety of azalea based on observations made of four year old plants grown in ground in a part shade trial planting and three-year-old plants grown in trade and three-gallon containers according to wholesale commercial production conditions, under full-sun and in an evaluation bed under semi-shade conditions in Dearing, Ga. in the spring, summer, and fall seasons of 2009, 2010, and 2011. The colors of the various plant parts are detailed with reference to The Royal Horticultural Society Colour Chart (2001).

Classification:

*Family*.—Ericaceae.

*Species*.—*Rhododendron* sp.

*Common name*.—Azalea.
*Denomination*.—'MNIHAR023'.

Parentage:
*Female parent*.—Unknown.
*Male parent*.—Unknown.

Plant:
*Form*.—Compact, dense, broadly globose.
*Texture*.—Medium.
*Height*.—76.2 cm to 106.68 cm.
*Width*.—121.92 cm to 152.4 cm.
*Growth habit*.—Freely branching; dense and compact in nature.
*Growth rate*.—Moderate growth rate under normal fertilization and moisture conditions. In a period of 4 years from a rooted cutting the plant reaches a height of 36.0 cm and a spread of 66.0 cm. The growth rate is normally averages about 18.0 cm per year; the plant reaches a height of 76.2 cm to 106.68 cm at maturity while maintaining an compact, dense habit due to the abundant branch development.
*Spring growth*.—The date of initial spring growth is April 1, followed by continuous growth through fall.
*Life cycle*.—Perennial and evergreen.

Leaves:
*Arrangement*.—Alternate, simple, pubescent, and evergreen.
*Shape*.—Oblanceolate to elliptic.
*Apex*.—Mucronate.
*Base*.—Attenuate.
*Margin*.—Entire.
*Length*.—3.5 cm.
*Width*.—1.9 cm.
*Venation pattern*.—Pinnate; the mid-veins and laterals are impressed on the upper surface and the prominent on the lower surface.
*Immature leaf upper surface*.—Color: Matte, RHS 144A (yellow-green). Pubescence: Moderate amount of strigose. Pubescence color: RHS 164C (greyed-orange) to RHS 164B (greyed-orange).
*Immature leaf lower surface*.—Color: Matte, RHS 147C (yellow-green). Pubescence: Moderate amount of strigose. Pubescence color: RHS 155C (white) and RHS 164A (greyed-orange), with the majority being RHS 155C.
*Mature leaf upper surface*.—Color: Glossy, RHS 147A (yellow-green). Pubescence: Moderate amount of strigose. Pubescence color: RHS 164B (greyed-orange).
*Mature leaf lower surface*.—Color: Matte, RHS 147B (yellow-green). Pubescence: Moderate amount of strigose. Pubescence color: RHS 164B (greyed-orange).
*Petiole*.—Length: 0.6 cm to 0.9 cm. Diameter: 0.1 cm by 0.15 cm. Pubescence: Strigose, moderate amount. Length: 0.08 cm. Color: Immature: RHS 164B (greyed-orange). Mature: RHS 166B (greyed-orange). Color: Immature: RHS 146D (yellow-green). Mature: RHS 147C (yellow-green).

Stems:
*Form*.—Branched at terminal buds and from some axillary buds at leaf nodes.
*Young stems* (*Actively growing, less than one year old*).—Color: RHS 144B (yellow-green). Pubescence: Strigose. Pubescence color: Begins RHS 164D (greyed-orange) maturing to RHS 165B (greyed-orange). Length of fully elongated flush: 3.3 cm. Diameter: 1.5 cm.
*Mature stems* (*One year old and older*).—Color: RHS 200A (brown) and RHS 200C (brown). Pubescence: Strigose. Pubescence color: RHS 200C (brown). Length: 11.0 cm on average for a full year's growth. Diameter: 0.3 cm in second year. Pith: Solid and uniform. Internode length: 1.3 cm.

Flower buds:
*Arrangement and form*.—At terminal; borne in groups of one or two flowers per bud with one, two, or three buds per terminal, buds sheathed by one or two modified leaf bracts.
*Bracts*.—Length: Average 1.6 cm. Width: 0.6 cm. Color: RHS 147A (yellow-green).
*Shape*.—Ovate.
*Apex*.—Acute.
*Base*.—Rounded.
*Length* (*at tight bud*).—1.3 cm.
*Diameter* (*at tight bud*).—0.6 cm.
*Color* (*of scales*).—Immature: RHS 144D (yellow-green). Mature: 146B (yellow-green) with areas of RHS 144A (yellow-green).
*Texture*.—Matte; strigose pubescence, moderate amount.
*Pubescence color*.—RHS N167B (greyed-orange).
*Pedicel*.—Length: 0.6 cm at point bud begins to open. Diameter: 0.15 cm. Texture: Pubescent, strigose pubescence, moderate amount. Pubescence color: RHS 161D (greyed-yellow) near base, RHS N155A (white). Color: RHS 144B (yellow-green).

Calyx:
*Calyx diameter*.—0.6 cm.
*Sepal length*.—0.5 cm.
*Sepal diameter*.—0.3 cm.
*Sepal quantity*.—5.
*Texture*.—Pubescent, strigose and villous pubescence mainly along the margin. Pubescence color: RHS N155A (white).
*Color*.—RHS 144A (yellow-green).

Flowers:
*Type*.—Perfect, single flowers.
*Shape*.—Open funnel-shaped.
*Flowering habit and period*.—Borne on the previous season's growth; Three weeks beginning in late April and sporadically starting in October continuing until frost in Dearing, Ga.
*Lastingness of flowers on the plant*.—4 to 5 days in the sun; 4 to 6 days in the shade.
*Fragrance*.—Absent.
*Diameter*.—5.9 cm.
*Depth*.—3.8 cm.
*Petals*.—Quantity per flower and arrangement: 5 imbricate petals that are fused at the base and remain fused up to 2.0 cm from the base. Shape: Obovate. Apex: Rounded. Base: Fused. Margin: Entire, slightly wavy to crisped. Texture (both surfaces): Glabrous. Length (of petals without spots): 4.4 cm. Width (of petals without spots): 3.3 cm. Length (of petals with spots): 4.5 cm. Width (of petals with spots): 3.5 cm. Color: Upper surface: One half of petal on apex end RHS 51D (red) with RHS 51B (red) spots, one half of petal nearest the center of the flower RHS 157C (green-white) with RHS 51B (red) spots. Lower surface: One half of petal on apex end RHS 51D (red), one half of petal nearest the center of the flower RHS 157C (green-white). Spots are not visible on the lower surface.

Reproductive parts:

*Pistil*.—Quantity and form: Single, non-petaloid. Length: 3.8 cm. Diameter: 0.05 cm.

*Stigma*.—Color: RHS N144A (yellow-green). Diameter: 0.15 cm.

*Style color*.—RHS N155C (white).

*Ovary*.—Pubescent, strigose RHS N155A (white) with 5 locules. Color: RHS 143A (green).

*Stamens*.—Quantity: 5 per flower; non-petaloid. Filament length: 2.9 cm. Filament width: 0.05 cm. Color: The ½ to ⅓ of the stamen closest to the anther is RHS 69D (red-purple) and the rest of the stamen is N155A (white).

*Anther*.—Length: 0.4 cm. Width: 0.1 cm. Color: RHS 165B (greyed-orange). Pollen: Abundant. Color: RHS 155D (white).

Fruit and seed: Observed.

*Maturity*.—The capsule matures in about 6 months in Dearing, Ga. and the fruit set is low and contains about 100 to 150 non-winged seeds.

*Capsule length*.—0.5 cm.

*Capsule width*.—0.3 cm.

*Capsule color*.—RHS 146A (yellow-green).

CULTURE

'MNIHAR023' grows well in a wide range of conditions and tolerates sun to shade. 'MNIHAR023' prefers moist, well-drained soil that is rich in organic matter and responds well to mulching and medium applications of fertilizer. 'MNIHAR023' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Susceptible to lace bugs, root weevils, and spider mites. Fungal and bacterial pathogens have not been observed, but no resistance testing has been performed.

COMPARISON WITH COMMERCIAL VARIETIES

In Table 1, 'MNIHAR023' is compared to commercial varieties 'Fascination' (unpatented) and 'Midnight Flare' (unpatented) which where utilized in the same hybridization program from which 'MNIHAR023' was developed.

TABLE 1

| Characteristic | 'MNIHAR023' | 'Fascination' | 'Midnight Flare' |
|---|---|---|---|
| Plant Height (Mature) | 76.2 cm to 106.68 cm | 106.68 cm | 106.68 cm |
| Flower Diameter | 5.9 cm | 11.43 cm | 7.62 cm |
| Flower Form | Single | Single | Single |
| Flower Color | Light peach with a light greenish center | Light pink with red border | Deep red |
| Bloom Period | Late April to Mid May and sporadically in October until frost | Mid-April to late April | April |
| Hardy Zone | 7 | 6 | 6 |
| Stamen Number | 5 | 5 | 5 |
| Stamen Type | Non-petaloid | Non-petaloid | Non-petaloid |

When 'MNIHAR023' is compared to the commercial variety 'Roblen' (U.S. Plant Pat. No. 16,248), 'MNIHAR023' has a compact, dense, broadly globose growth habit with a height of 36.0 cm and a spread of 66.0 cm in 4 years, while 'Roblen' has a height of 91.44 cm and a spread of 60.96 cm in six years. Additionally, 'MNIHAR023' produces light peach with a light greenish center flowers, while 'Roblen' has bright red flowers.

I claim:

1. A new variety of azalea plant named 'MNIHAR023' as herein shown and described.

* * * * *